(12) United States Patent
Larsson et al.

(10) Patent No.: US 6,524,289 B1
(45) Date of Patent: Feb. 25, 2003

(54) SECURING ARRANGEMENT FOR ABSORBENT ARTICLE

(75) Inventors: Björn Larsson, Billdal (SE); Nils Ljungqvist, Lidköping (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/529,801

(22) PCT Filed: Oct. 1, 1998

(86) PCT No.: PCT/SE98/01773

§ 371 (c)(1),
(2), (4) Date: Apr. 20, 2000

(87) PCT Pub. No.: WO99/20217

PCT Pub. Date: Apr. 29, 1999

(30) Foreign Application Priority Data

Oct. 20, 1997 (SE) .............................................. 9703802

(51) Int. Cl.[7] .................................................. A61F 13/15
(52) U.S. Cl. .................. 604/385.01; 604/365; 604/390; 604/391; 428/252; 428/156
(58) Field of Search ................................. 604/365, 390, 604/391, 385.01; 128/156; 428/252; 24/304

(56) References Cited

U.S. PATENT DOCUMENTS

| | | | |
|---|---|---|---|
| 3,888,255 A | | 6/1975 | Shah et al. |
| 4,376,440 A | | 3/1983 | Whitehead et al. |
| 4,654,254 A | * | 3/1987 | Gerry .......................... 428/252 |
| 5,636,414 A | * | 6/1997 | Litchholt ...................... 24/304 |
| 6,213,991 B1 | * | 4/2001 | Kling .................... 604/385.01 |

FOREIGN PATENT DOCUMENTS

| | | |
|---|---|---|
| EP | 0 234 194 | 9/1987 |
| EP | 0 393 953 | 10/1990 |
| EP | 0 471 385 | 2/1992 |
| EP | 0 471 386 | 2/1992 |
| EP | 0 471 387 | 2/1992 |
| EP | 0 737 462 | 10/1996 |
| GB | 791749 | 3/1958 |

* cited by examiner

*Primary Examiner*—John J. Calvert
*Assistant Examiner*—Angela J. Grayson (57) ABSTRACT

An absorbent article, such as a sanitary towel, an incontinence protector, a diaper, a seat protector or a bed protector, includes an absorption body enclosed between a liquid-permeable cover layer and a liquid-tight cover layer, which liquid-tight cover layer includes a carrier layer having a first surface and a second surface, the first surface being intended to function as a securing arrangement for securing on a textile surface or textile-like surface. The securing arrangement has a multiplicity of individual fibers, which are free from one another and each have two fiber ends, are secured via one fiber end to the first surface of the carrier layer, and moreover by the fact that the first surface, in order to serve as a securing surface against a textile material surface or textile-like material surface, is at least partially coated with an adhesive.

17 Claims, 4 Drawing Sheets

SECURING ARRANGEMENT FOR ABSORBENT ARTICLE

TECHNICAL FIELD

The present invention relates to an absorbent article, such as a sanitary towel, an incontinence protector, a diaper, a seat protector or a bed protector, comprising an absorption body enclosed between a liquid-permeable cover layer and a liquid-tight cover layer, which liquid-tight cover layer comprises a carrier layer having a first surface and a second surface, the first surface being intended to function as a securing arrangement for securing on a textile surface or textile-like surface. The invention also includes a diaper with a securing arrangement according to the invention, for fastening the article in a shape similar to pants.

BACKGROUND

The most common way of securing a sanitary towel inside a pair of pants during use is to arrange a securing surface, in the form of a self-adhesive, on that side of the sanitary towel which, during use, is intended to be in contact with the user's pants. In order to avoid problems associated with the stickiness of the adhesive surface during storage and transport of the sanitary towels, the securing adhesive is usually protected by a separate detachable strip of paper or the like which has been treated with a release agent. When the sanitary towel is to be used, the protective strip is removed so that the adhesive is exposed and can be used for securing the sanitary towel in the user's pants. The protective strip fulfils no other function and is thrown away once it has been detached from the securing adhesive. The use of such protective strips involves a number of disadvantages. For example, it is awkward to handle the protective strips when the sanitary towel is to be used, especially if the sanitary towel is provided with several different protective strips which need to be removed. In addition, the use of protective strips means that a lot of material is unnecessarily used up, which is a disadvantage from the environmental and energy points of view and also from the point of view of cost.

A further inconvenience with a self-adhesive placed on the liquid-tight cover layer for securing the article to the pants is that it is difficult to place the article inside a pair of pants without the article folding or deforming during positioning. The folding or deformation can lead to adhesive coming into contact with adhesive. These articles are then very often unusable, since it is difficult to free the stuck contact areas from each other without destroying the article. If an article in this condition is still used, there is a high risk of liquid leaking out. The problem is associated principally with incontinence protectors and other articles used by the elderly or handicapped persons with reduced mobility of the hands, but the problem also arises when using sanitary towels.

In order to eliminate the separate protective strips, it is already known to provide a sanitary towel both with adhesive areas and with areas which have been treated with release agent, these being arranged in such a way that the sanitary towel can be folded up with the adhesive areas bearing against, and protected by, the areas which have been treated with release agent. Sanitary towels of this kind are described in U.S. Pat. No. 4,376,440, EP 471,385, EP 471,386 and EP 471,387. Such an arrangement reduces the amount of material used up, and to some extent simplifies the handling of the sanitary towel. An important problem, however, is that the possibility of arranging the securing adhesive in the manner which affords the best attachment of the sanitary towel inside the user's pants is greatly restricted since the positioning of the adhesive surfaces must in the first instance be chosen in such a way that, after the sanitary towel has been folded up, the adhesive surfaces bear against the corresponding areas that have been treated with release agent. In addition, there is still the problem of the article folding as it is being placed in the pants, resulting in undesired sticking together of the adhesive surfaces.

EP 393,953 has already disclosed a pressure-sensitive securing arrangement which comprises a support whose one side is provided with a pressure-sensitive adhesive, arranged in the spaces between a number of barbs or projections protruding from the support, the barbs or projections extending beyond the adhesive. The securing arrangement is particularly suitable for use on fabrics, the barbs or projections being able to penetrate down through the surface of the fabric so that the adhesive is brought into contact with and sticks to the fabric. The disadvantages of this known type of securing arrangement are mainly that it is stiff and hard and thus can easily cause chafing and other discomfort for the user. In addition, the protruding barbs pose a certain risk of damage to the surface on which the arrangement is secured. Moreover, the securing arrangement is relatively expensive and complicated to produce. A similar adhesive securing arrangement is described in U.S. Pat. No. 4,376,440.

Another sanitary towel having an adhesive securing arrangement is described in EP 234,194 and in EP 229,639. The known sanitary towel comprises a pressure-sensitive adhesive securing layer, and an elastic foam material layer arranged outside the adhesive layer and provided with openings through which the adhesive is exposed for securing purposes. Such a securing arrangement, however, does not have a sufficiently large available securing surface area to permit satisfactory securing. Moreover, there are difficulties involved in producing the known sanitary towel, since a web of foam material is relatively fragile and easily breaks when subjected to the tensile stresses that arise at high production speeds. In addition, at high production speeds, it is difficult to monitor and control the stretching which occurs in the elastic foam material. Moreover, the foam material is expensive and difficult to produce in the form of layers that are sufficiently thin to allow the adhesive to act through the foam material. A thick, bulky material is also difficult to handle in a continuous process since it requires frequent roller changes, which of course has a negative impact on efficiency and cost.

An adhesive securing arrangement for securing a sanitary towel inside a pair of pants is also described in U.S. Pat. No. 3,888,255. The securing arrangement comprises an elastic foam material layer having a coefficient of friction greater than 2. A pressure-sensitive adhesive layer is arranged on the elastic foam material layer. Such a securing arrangement, however, requires a separate detachable protective strip of paper or the like that has been treated with release agent. Also, it is difficult to free adhering contact areas from each other if the article becomes folded during actual securing in the pants.

Another problem with the previously known sanitary towels having a securing arrangement in the form of a self-adhesive coating is that it is difficult to regulate the degree of stickiness so that the latter is sufficient regardless of what material the user's pants are made of. The stickiness will be different for different textile materials, and one and the same adhesive coating will, for example, secure several times better against a surface made of nylon, or nylon-like material, than against cotton material. In the case of an adhesive coating which provides sufficiently good securing in pants made of cotton, there is a risk that a pair of pants made of nylon or the like will be damaged when the sanitary towel is removed, or that residues of adhesive will remain on the pants.

Diapers of the type mentioned at the outset are usually secured with tape flaps which are secured against a reinforced plastic surface on the front portion of the diaper. Although such a securing arrangement provides satisfactory securing of the diapers, it also has some disadvantages. For example, it is difficult to protect the tape flaps before use. In the known diapers, this problem is solved by the fact that the flaps are folded in over surfaces that have been treated with release agent, either on the tapes themselves or on the diaper. Folded tapes are expensive and difficult to produce and arrange on the diapers and are the cause of a relatively large proportion of the waste which arises in the manufacture of the diapers. In addition, it can be difficult to release the tape from the surface treated with release agent when the diaper is to be used. Particularly in cases where the diaper is to be placed on an extremely lively child, flaps that are difficult to open can be a nuisance. To increase the ease of handling of the tape flaps, these are made of fairly stiff material, which easily gives rise to sharp corners and edges that can cause chafing and irritation to the user's skin. Another arrangement for securing a diaper round the user's waist is to use mechanical securing members such as, for example, velcro-type seals. The disadvantage of such securing members is, however, that they are expensive to produce. Moreover, they have a relatively high rigidity, which can cause chafing and irritation to the user's skin.

DESCRIPTION OF THE INVENTION

The present invention provides an absorbent article, such as a sanitary towel, an incontinence protector, a diaper, a seat protector or a bed protector, which, during use, is very soft and pliable and does not cause chafing. The absorbent article also provides good securing against textile surfaces or textile-like surfaces.

The absorbent article comprises an absorption body enclosed between a liquid-permeable cover layer and a liquid-tight cover layer, which liquid-tight cover layer comprises a carrier layer having a first surface and a second surface, of which the first surface functions as a securing arrangement for securing on a textile surface or textile-like surface, and is distinguished primarily by the fact that a multiplicity of individual fibres, which are free from one another and each have two fibre ends, are secured via one fibre end to the first surface of the carrier layer, and moreover by the fact that the first surface, in order to serve as a securing surface against a textile material surface or textile-like material surface, is at least partially coated with an adhesive.

With a securing arrangement, for an absorbent article, comprising a multiplicity of fibres, a soft securing arrangement is obtained which is discreet and easy to wear and which does not cause chafing against the user.

The degree of sticking to a textile surface or textile-like surface can be varied, not only through the amount and choice of adhesive, but also through the choice of fibres, fibre density, and length of the fibres. This makes it possible to obtain an adhesion which is suitable for different types of textile surfaces or textile-like surfaces. In addition, it is possible to have a very thin adhesive layer, or a not completely covering adhesive layer, since the individual fibres themselves give the surface of the securing arrangement greater friction than does an essentially smooth surface without fibres. It is therefore not necessary for all the fibres on the fibre surface to have an adhesive coating.

A discontinuous, not completely covering adhesive layer can be obtained, for example, by spraying the adhesive onto the support in the form of small drops or fibres. In addition, the desired adhesion can be obtained by means of only certain areas or zones of the total surface being coated with adhesive. A not completely covering adhesive layer eliminates the need for a separate detachable strip of material for protecting a securing adhesive surface during storage and transport.

Another advantage of the securing arrangement is that the risk of the pants being damaged when the article is being removed, or of residues of adhesive being left behind, is almost completely eliminated. In addition, with such a securing arrangement, it is easy to adjust the position of the article if the article ends up in the wrong position at the time of securing or becomes folded or displaced during use.

A further advantage of the present securing arrangement is that it is relatively simple to produce. The fibres are preferably oriented against a carrier layer by a flocking technique. The fibres are secured to the carrier layer by gluing, or by means of at least one component in the carrier material or in the fibres being heated during the flocking procedure to a temperature in excess of the melt temperature of the component.

According to one embodiment, the adhesive is a self-adhesive. The securing on the textile surface or textile-like surface is thus obtained both mechanically, by means of the fibre surface having a high degree of friction on the textile surface, and also adhesively, by means of the securing surface being completely or partially coated with the self-adhesive. Thus, with such a securing arrangement, it is possible to obtain a softer and more pliable securing arrangement compared to exclusively mechanical securing arrangements, such as various types of velcro closures. In addition, there is no need, as there is in the case of purely adhesive securing arrangements, to provide a separate detachable strip of material for protecting the securing adhesive surface prior to use.

One embodiment is characterized in that the carrier layer is coated with a self-adhesive, after which the multiplicity of individual fibres are applied and secured on the adhesive-coated surface of the carrier layer. According to this embodiment, therefore, the applied fibres do not have any adhesive coating. The advantage of such an embodiment is that the self-adhesive is protected from undesired contact with other material by means of the applied fibre layer which creates a distance between the adhesive layer and other contact surfaces. On sticking to a textile-like material, however, the self-adhesive layer arranged under the fibres functions to increase the stickiness by means of contact being obtained between the receiving material and the self-adhesive layer when an external pressure is applied. A further advantage of such an embodiment is that the adhesive, apart from strengthening the securing of the article during use, also secures the fibres to the carrier layer surface during the actual application of the fibres. In this way, a further adhesive for securing the fibres is eliminated.

According to another embodiment, the adhesive is applied after the fibres have been arranged on the carrier layer, for example by spraying the adhesive onto the fibre-coated surface. This creates a non-covering adhesive layer on the fibre surface. An advantage of such an embodiment is that no great pressure needs to be applied to secure a receiving material to such a securing arrangement. In addition, there is very little risk of the pants being damaged when the article is being removed or of residues of adhesive being left behind.

It is advantageous if the adhesive secures at least to the free, outer end of the fibres. In such an embodiment, it is also possible for the adhesive to be one which solidifies after application. The idea of this embodiment is that the adhesive is applied so that it binds on the fibre surface and creates an uneven surface structure presenting small projections of applied adhesive along the fibre surface on the outer, free fibre end, or, alternatively, along the entire fibre surface. These projections provide increased mechanical securing against a textile-like surface.

In order to increase the mechanical securing capacity, it is also possible to use fibres having a curved fibre end. These curved fibre ends are obtained, for example, by the free fibre end of the fibres being heated to the softening point of the fibres, or to the melt temperature of the fibres. This creates curved fibre ends or, alternatively, a melted fibre edge which has a deformed, hook-like end portion. A curved fibre end or melted edge increases the possibility of the securing arrangement hooking securely in a textile-like material.

According to another embodiment, the first surface of the carrier layer has certain areas which are free from fibres. Such an embodiment is advantageous for increasing the adhesive securing capacity for a securing arrangement having an adhesive-coated carrier layer, and fibres which are not adhesive-coated. If the first surface of the carrier layer also has small surfaces which are free from secured fibres, the free adhesive-coated surface is protected by the fibres which are secured around the free fibre surface. This means that no separate detachable strip of material is needed for protecting the adhesive securing surface prior to use. Another advantage of such an embodiment is that the consumption of fibres is reduced. A further advantage of such an embodiment is that it is possible to create a specific, desired pattern and thereby achieve an aesthetically pleasing appearance of the surface of the securing arrangement.

According to one advantageous embodiment, the carrier layer also constitutes the liquid-tight cover layer of the article. The carrier layer thus consists of a liquid-tight material layer, such as, for example, a plastic film. The advantage of such an embodiment is that a joining bridge between the liquid-tight cover layer and the carrier layer is eliminated. The material consumption is also reduced, which is of importance from the point of view of cost as well as from the environmental aspect. It is also possible to produce an article which is softer and more pliable than when separate material layers are used as a liquid-tight cover layer and a carrier layer.

The invention also includes a diaper comprising a first, liquid-permeable cover layer, and a second, liquid-tight cover layer, which two cover layers are connected to each other around an absorption body enclosed between the cover layers. The diaper has a front portion, a rear portion, and a crotch portion situated between these two portions, and moreover two longitudinal side edges and a front waist margin and a rear waist margin, which two waist margins are designed to surround a user's waist and thus form the waist opening of the diaper. The diaper moreover comprises at least one fastening arrangement for fastening the article in a shape similar to pants, the fastening arrangement comprising a first component member and a second component member arranged at each side edge, the component members being designed to cooperate with each other for fastening the article. The securing arrangement is distinguished primarily by the fact that at least the first component member comprises a carrier layer having a first surface and a second surface, the first surface being intended to cooperate with the second component member for fastening the article, and against which surface a multiplicity of individual fibres, which are free from one another and each have two fibre ends, are secured via one fibre end, and by the fact that the first surface, in order to serve as a securing surface against a textile material surface or textile-like material surface, is coated with an adhesive. The design of the first component member for securing the diaper in a shape like pants by means of a securing arrangement according to the invention also covers all embodiments in the descrtiption and claims.

According to one embodiment, the second component member also consists of a carrier layer against which a multiplicity of individual fibres are secured via one fibre end. The second component member is either adhesive-coated or free from such adhesive coating. An advantage of adhesive-coated second component members is that an increased adhesive securing capacity is achieved. In addition, such a diaper is easier to produce, since only one securing material is used. Nevertheless, from environmental considerations, it may be more advantageous to have second component members which are free from adhesive.

BRIEF DESCRIPTION OF THE FIGURES

The invention will be described in greater detail hereinbelow with reference to the figures which are shown on the attached drawings.

DESCRIPTION OF ILLUSTRATIVE EMBODIMENTS

Figure 1:
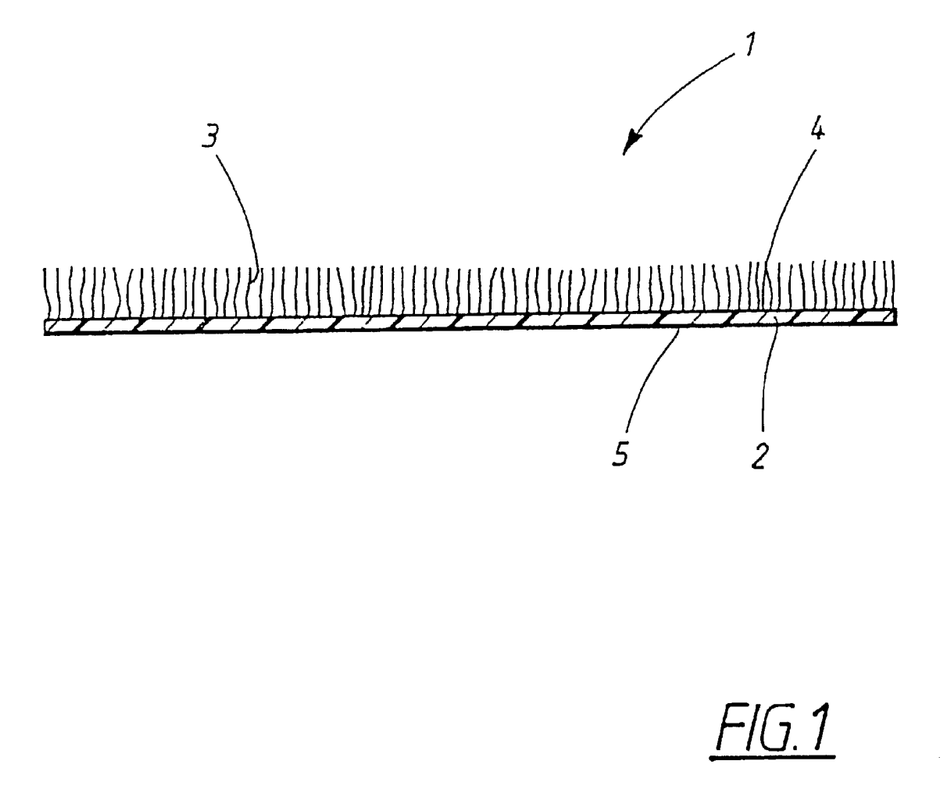
FIG. 1 shows a perspective view of a securing arrangement according to the invention, arranged in the crotch area of a pair of pants.

The securing arrangement 1 shown in FIG. 1 comprises a carrier layer 2 which has a first surface 4 and a second surface 5. A multiplicity of individual fibres 3 are secured via one fibre end on the first surface 4 of the carrier layer. Moreover, the first surface 4, in order to serve as a securing surface against a textile material surface or textile-like material surface, is coated with an adhesive.

The carrier layer 2 preferably consists of a plastic film, but it can of course also consist of a nonwoven material, a foam material or any other material or laminate suitable for the purpose. The fibres 3 consist, for example, of polypropylene, polyethylene, polyester, viscose or cotton. Of course, the invention is not limited to these fibre materials, and, instead, other materials suitable for the purpose can also be used. In order to achieve a desired optimum friction against a textile surface or textile-like surface, the length and width of the fibres can be varied. The fibre length is preferably between 0.7 and 2 mm. Moreover, the fibres can stick up at different heights because of irregularities in the carrier material, and because the angle between the carrier material and the individual fibres varies.

The adhesive is applied to the carrier layer 2 either before application of the fibres 3 on the first surface 4 of the carrier layer, or after the fibres have been applied to the carrier layer. When the adhesive is applied to the carrier layer 2 before the fibres 3, the adhesive consists of a self-adhesive which, upon contact with the receiving material, increases the sticking capacity. If, on the other hand, the adhesive is applied after the fibres 3 have been secured on the surface via one end, it is also possible to use an adhesive which solidifies. In these cases the adhesive is applied to the fibre surface in order to create an uneven surface structure, either along parts of the fibre surface or along the entire fibre surface. These irregularities, which are created by the adhesive solidifying and forming small portions projecting from the fibre surface, result in an increase in the mechanical securing on a textile surface.

The adhesive is applied for example by spraying it onto the surface. By using a spray technique, it is possible to obtain a thin and non-covering adhesive layer. It is also possible to obtain a desired, specific adhesive strength by controlling the amount of adhesive that is applied.

In order to increase the mechanical securing, it is also possible to use fibres 3 having a curved shape near the free, outer fibre end. The curved fibre end results in an increased mechanical securing capacity. The curved fibre ends are obtained by means of the fibres being heated at the ends to the softening temperature of the fibre material. It is also possible to heat the fibres to the melt temperature of the fibre material and thereby to create a melted outer fibre edge. After cooling, such a fibre edge has solidified hook-shaped elements which increase the ability of the material to hook onto a textile material.

Figure 2:
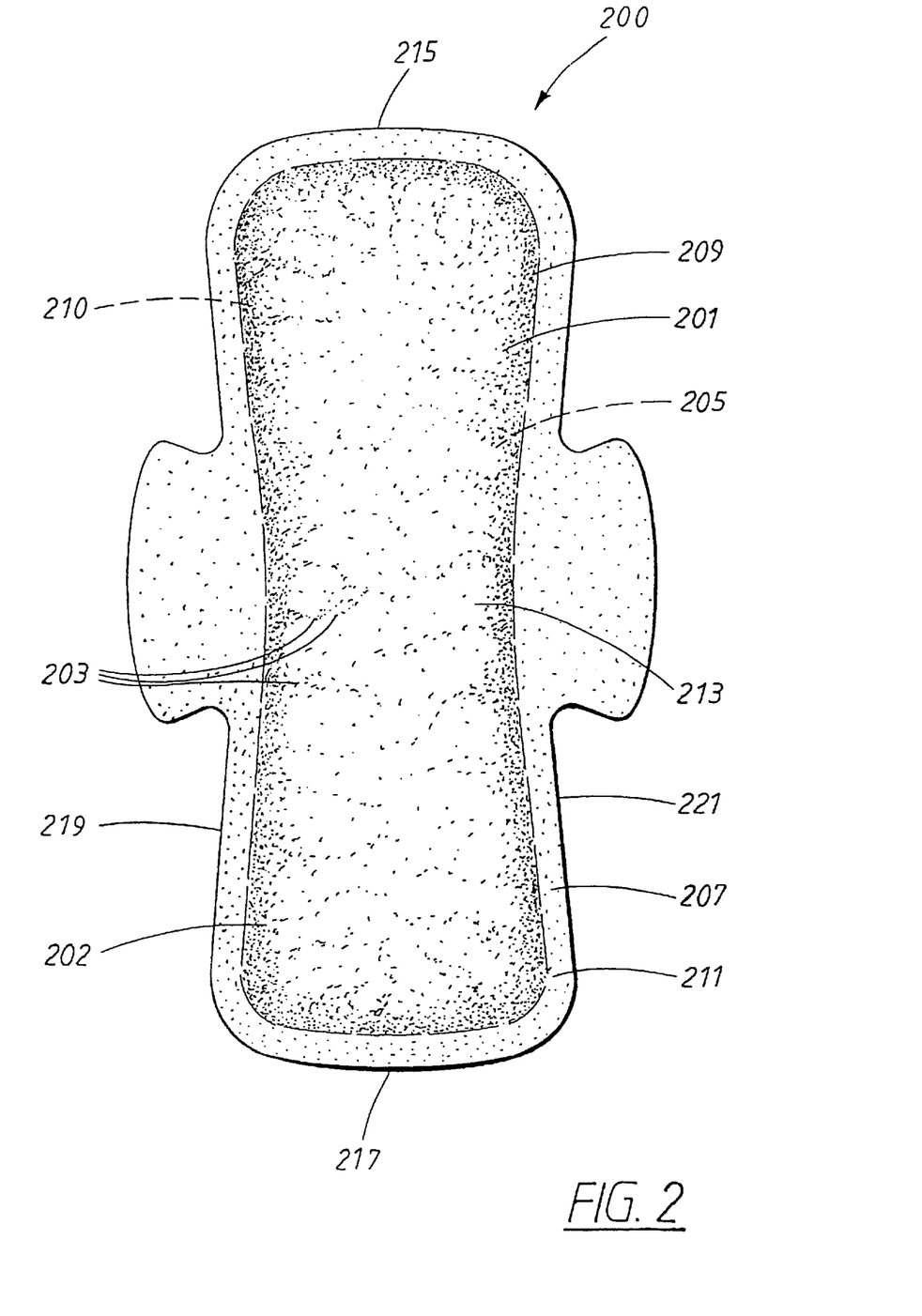
FIG. 2 shows a sanitary towel with a securing arrangement according to the invention, seen from the side which, during use, is intended to be directed away from the user.

The sanitary towel 200 shown in FIG. comprises a liquid-permeable cover layer 210, a liquid-tight cover layer 202, and an absorption body 205 enclosed between the cover layers 210, 202. The two cover layers have a somewhat greater planar extent than the absorption body 205 and extend a distance beyond the edges of the absorption body 205, around its periphery. The cover layers are connected to one another within the protruding portions 207, for example by gluing or welding with ultrasound or heat.

The liquid-permeable cover layer 210 usually consists of a perforated plastic film, a nonwoven layer or a laminate thereof.

The absorption body 205 is usually made up of one or more layers of cellulose fibres, for example cellulose pulp. The absorption body 205 can also include, in addition to cellulose fibres, superabsorbent material, i.e. material in the form of fibres, particles, granules, films or the like, which is able to absorb liquid corresponding to several times the superabsorbent material's own weight. Superabsorbent material binds the absorbed liquid and forms a liquid-containing gel. The absorption body 205 can also comprise binders, shape-stabilizing components or the like. Further absorption layers which improve the absorption characteristics can also be used, such as various types of liquid-spreading inserts or material layers. The absorption body 205 can be treated chemically or physically in order to alter the absorption characteristics. For example, it is common to provide an absorption layer with compressions in order to control the flow of liquid in the absorption body 205. In addition, other types of absorption material can be used, alone or in combination with cellulose fibres and superabsorbent material. Examples of absorbent materials which can be used are absorbent nonwoven material, foam or the like.

In the sanitary towel 200 shown in FIG. 2, the liquid-tight cover layer 202 consists of a plastic film, which plastic film also constitutes the carrier material for the securing arrangement 201 of the sanitary towel 200. The securing arrangement 201 is constructed in the same way as the securing arrangement 1 shown in FIG. 1. Thus, the securing arrangement 201 has a carrier material and a multiplicity of fibres 203 which are secured via one end to the carrier material. In addition, the securing arrangement 201 is coated with a not completely covering adhesive layer. However, it is alternatively possible for the liquid-tight cover layer 202 and the carrier layer of the securing arrangement 201 to consist of two different material layers. For example, the liquid-tight cover layer 202 can consist of a hydrophobic fibre fabric, a foam material or some other liquid-tight layer of material. In addition to consisting of various film materials, the carrier layer can also consist of of a nonwoven layer, a foam material or some other material suitable for the purpose.

The sanitary towel 200 is hourglass-shaped, with wider end portions 209, 211 and a narrower crotch portion 213 situated between the end portions 209, 211. The crotch portion 213 is that part of the sanitary towel that is intended, during use, to be arranged in the user's crotch area and to serve as a receiving surface for the body fluid which is excreted onto the sanitary towel. The sanitary towel also has two transverse end edges 215, 217 and two longitudinal side edges 219, 221.

Figure 3:
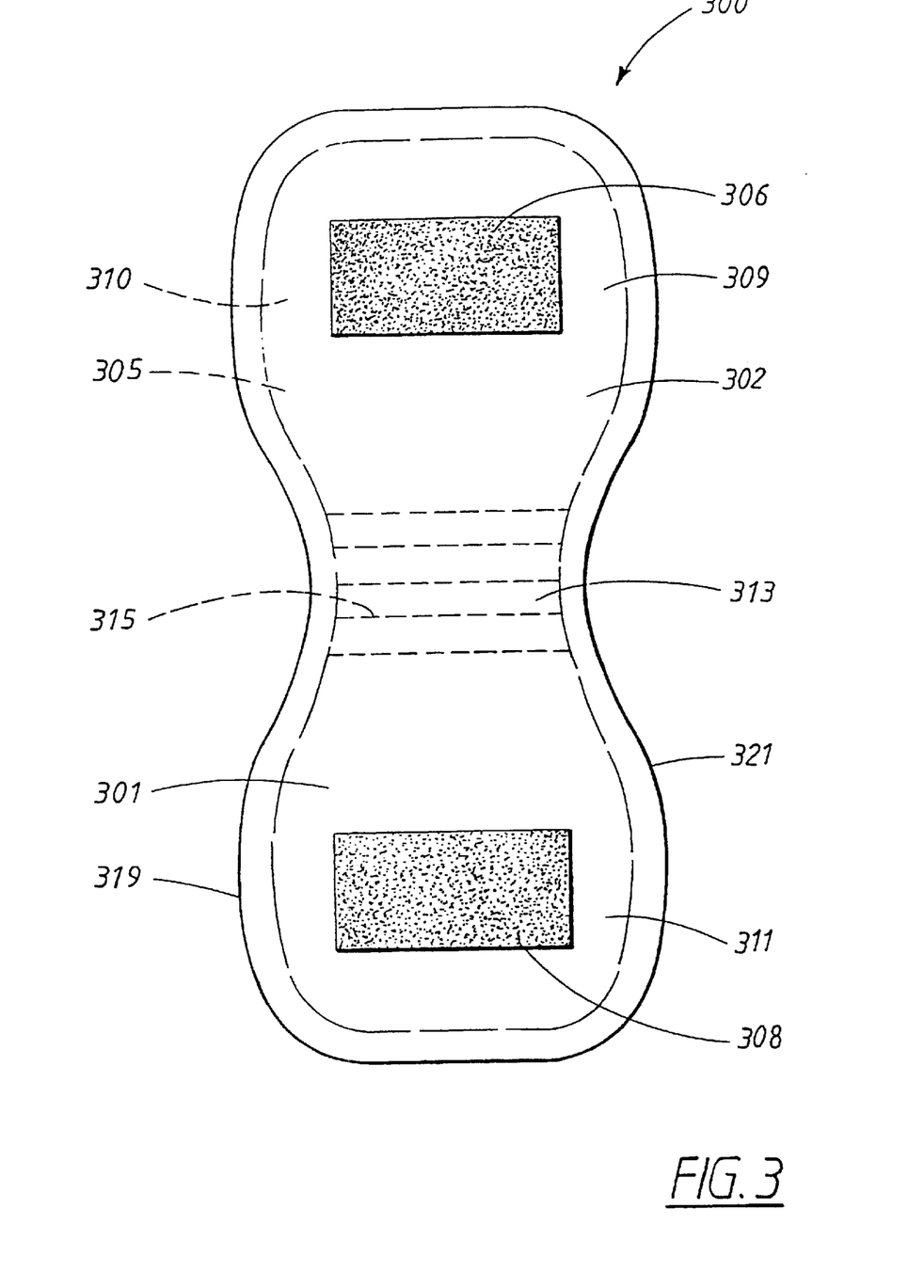
FIG. 3 shows an incontinence protector with a securing arrangement according to the invention, seen from the side which, during use, is intended to be directed away from the user.

The incontinence protector 300 shown in FIG. 3 has essentially the same construction as the sanitary towel 200 shown in FIG. 2. Thus, the incontinence protector 300 has a liquid-permeable cover layer 310, a liquid-tight cover layer 302, and an absorption body 305 enclosed between the cover layers 310, 302. When the incontinence protector is to be used, it is arranged inside a user's pants, with the liquid-permeable cover layer 310 directed towards the user, and with the liquid-tight cover layer 302 directed towards the pants.

The incontinence protector 300 is also essentially hourglass-shaped, with two end portions 309, 311 and a narrower crotch portion 313 situated between the two end portions 309, 311. Transverse elastic members 315 in the form of strings, bands or the like are arranged in the crotch portion 313, between the two longitudinal side edges 319, 321. The elastic members 315 are arranged between the liquid-permeable cover layer 310 and the absorption body 305, but they can of course also be arranged within the absorption body 305, or on the liquid-tight cover layer 302.

Two securing arrangements 306, 308 are arranged on the liquid-tight cover layer 302 of the incontinence protector 300, one securing arrangement 306, 308 being arranged at either of the two end portions 309, 311 of the incontinence protector. The securing arrangements 306, 308 are constructed in the same way as the securing arrangements 1, 201 shown in FIGS. 1 and 2.

Figure 4:
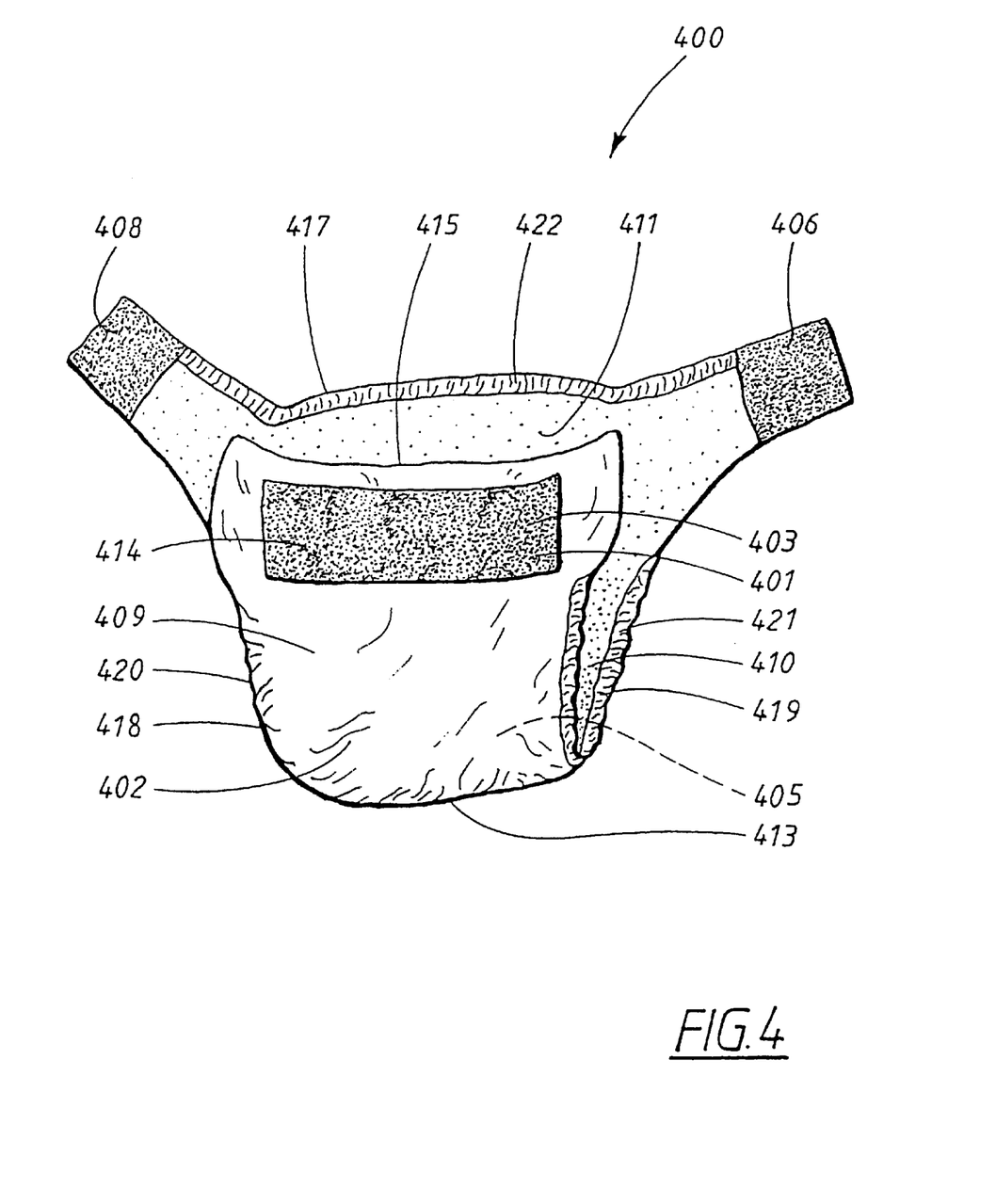
FIG. 4 shows a front view of a diaper.

The diaper 400 comprises a liquid-permeable cover layer 410, intended to be directed towards the wearer during use, a liquid-tight cover layer 402, intended to be directed away from the wearer during use, and an absorption body 405 enclosed between the two cover layers. The diaper 400 is designed in such a way that, during use, it surrounds the lower part of the user's trunk in the same way as pants. Thus, the diaper 400 has a front portion 409, a rear portion 411, and a narrower crotch portion 413 situated between the front portion and the rear portion. In addition, the diaper 400 has a front waist margin 415 and a rear waist margin 417 which together form the waist opening of the diaper.

The diaper 400 also comprises elastic members 418, 419 which are arranged along the longitudinal side edges 420, 421 of the diaper 400 and form elastic leg margins when the diaper is being used. The diaper 400 also comprises elastic members 422 arranged along the rear waist margin 417 of the diaper. on the longitudinal side edges 420, 421, on the rear portion 411 of the diaper, fastening flaps 406, 408 are arranged near the rear waist margin 417. The fastening flaps 406, 408 consist of a carrier layer arranged on the rear portion of the diaper, on which carrier layer a multiplicity of individual fibres 403 are secured via one of their fibre ends to the carrier layer. It is also possible for the fastening flaps 406, 408 to have a not completely covering adhesive-coated surface in order to increase the securing to the securing member 401. However, the fastening flaps 406, 408 can alternatively consist of any other soft, textile or textile-like material which can cooperate with a securing member 401, in accordance with the invention, arranged on the front portion 409 of the diaper.

The securing member 401 consists of a carrier layer which is arranged on the front portion 414 of the diaper, and against which carrier layer a multiplicity of individual fibres 403 are secured via one fibre end. In order to serve as a securing surface for the fastening flaps 406, 408, the securing arrangement 401 is coated with an adhesive. The securing arrangement 401 can consist of any of the embodiments set out in the description and claims.

Since the securing arrangement 401 forms an elongate securing area along the greater part of the front waist margin 415 of the diaper, it is possible to adapt the size of the waist opening to the user's body so that the best possible fit is achieved.

It is also possible instead to arrange securing members on the fastening flaps, in which case these cooperate with a textile-like receiving surface on the front portion of the diaper. In such an embodiment, the receiving surf ace can be made of any size and can, for example, extend across the entire liquid-tight cover layer of the diaper, as a result of which the fastening flaps can be secured anywhere on the outside of the diaper. This therefore provides greater possibilities of individually adapting the diaper to the user's body. In addition, after use, the diaper can be rolled or folded up into a package, the fastening flaps serving as sealing members for the package.

It is also possible to use a securing arrangement according to the invention for securing bed protectors or seat protectors against textile surfaces and for securing absorbent inserts inside special triangular cloths or diaper shorts.

A number of further application areas are also conceivable within the scope of the patent claims.

What is claimed is:

1. Absorbent article with a single-portion fastening surface, comprising:
   an absorption body (205; 305; 405) enclosed between a liquid-permeable cover layer (210; 310; 410) and a liquid-tight cover layer (202; 302; 402); and
   a single-portion fastening surface located on an external surface of the liquid-tight cover layer (202; 302; 420) in a region intended to come into contact with a wearer's undergarment,
   the single-portion fastening surface comprising a carrier layer (2) having a first surface (4) and a second surface (5),
   the first surface (4) at least partially coated with an adhesive, which adhesive functions as a securing arrangement (1; 201; 306, 308; 406, 408) for securing on a material surface of the undergarment, and
   a multiplicity of individual fibres (3; 203; 303; 403), which are free from one another and each have two fibre ends, secured via one fibre end to the first surface (4) of the carrier layer (2).

2. Absorbent article with a securing arrangement (1) according to claim 1, characterized in that the multiplicity of individual fibres (3) have an adhesive coating.

3. Absorbent article with a securing arrangement (1) according to claim 2, characterized in that the adhesive attaches to the free, second end of the fibres (3), or in the immediate vicinity of said free, second end, and forms adhesive projections sticking out from the surface of the fibres (3).

4. Absorbent article with a securing arrangement (1) according to claim 1, characterized in that the first surface (4) of the carrier layer (2) is coated with adhesive.

5. Absorbent article with a securing arrangement (1) according to claim 1, characterized in that the adhesive coating constitutes a not completely covering adhesive layer surface.

6. Absorbent article with a securing arrangement (1) according to claim 1, characterized in that the adhesive is a self-adhesive.

7. Absorbent article with a securing arrangement (1) according to claim 1, characterized in that the fibres (3) have a curve at the free fibre end.

8. Absorbent article with a securing arrangement (1) according to claim 1, characterized in that the fibres (3) have a fused material edge at the free fibre end.

9. Absorbent article with a securing arrangement (1) according to claim 1, characterized in that the first surface (4) of the carrier layer (2) has areas which are free from individually secured fibres (3).

10. Absorbent article with a securing arrangement (1) according to claim 1, characterized in that the carrier layer (2) constitutes the liquid-tight cover layer (202; 302) of the article.

11. Diaper according to claim 1, comprising a first, liquid-permeable cover layer (410), a second, liquid-tight cover layer (402), which two cover layers (410, 402) are connected to each other around an absorption body (405) enclosed between the cover layers, and having a front portion (409), a rear portion (411), and a crotch portion (413) situated between these two portions (409, 411), and moreover having two longitudinal side edges (420, 421) and a front waist margin (415) and a rear waist margin (417), which two waist margins (415, 417) are designed to surround a user's waist and thus form the waist opening of the diaper, and moreover comprising at least one further fastening arrangement for fastening the diaper in a shape similar to pants, the further fastening arrangement comprising first component members (401) and second component members (406, 408) arranged at each side edge (420, 421), the component members (401, 406, 408) being designed to cooperate with each other for fastening the article.

12. Diaper with a securing arrangement according to claim 11, characterized in that the second component member (406, 408) consists of a carrier layer having a first surface and a second surface, against which first surface a multiplicity of individual fibres, which are free from one another and each have two fibre ends, are secured via one fibre end, and the second component member (406, 408) is intended to serve as the receiving material surface for the first component member (401).

13. Absorbent article of claim 1, wherein the article is in the form of a sanitary towel, an incontinence protector, a diaper, a seat protector, or a bed protector.

14. A sanitary napkin, comprising:

an absorption body enclosed between an upper liquid-permeable cover layer and a lower liquid-tight cover layer; and a fastening surface located on an external surface of the liquid-tight cover layer in a region intended to come into contact with a wearer's undergarment, the fastening surface comprising a carrier layer having a first surface and a second surface, the first surface at least partially coated with an adhesive, which adhesive functions as a securing arrangement for securing on a material surface of the undergarment, and a multiplicity of individual fibres, which are free from one another and each have two fibre ends, secured via one fibre end to the first surface of the carrier layer.

15. The sanitary napkin of claim 14, wherein the second surface of the carrier layer contacts the external surface of the liquid-tight cover layer.

16. A incontinence protector, comprising:

an hourglass-shaped absorption body with two end portions and a crotch portion, the absorption body enclosed between an upper liquid-permeable cover layer and a lower liquid-tight cover layer; and a securing arrangement located on an external surface of the liquid-tight cover layer in each of the two end portions, each securing arrangement comprising a carrier layer having a first surface and a second surface, the first surface at least partially coated with an adhesive, which adhesive functions as a securing agent for securing on a material surface of the undergarment, and a multiplicity of individual fibres, which are free from one another and each have two fibre ends, secured via one fibre end to the first surface of the carrier layer.

17. The incontinence protector of claim 16, wherein the multiplicity of individual fibres is free of the adhesive coating the first surface.

* * * * *